United States Patent [19]

Morita et al.

[11] Patent Number: 4,571,384
[45] Date of Patent: Feb. 18, 1986

[54] METHANE PRODUCTION

[75] Inventors: Richard Y. Morita; Ronald D. Jones, both of Corvallis, Oreg.

[73] Assignee: State of Oregon acting by and through the State Board of Higher Education on behalf of Oregon State University, Eugene, Oreg.

[21] Appl. No.: 435,058

[22] Filed: Oct. 18, 1982

[51] Int. Cl.$^4$ .............. C12P 5/02; C12P 5/00; C12P 1/04; C12N 1/20
[52] U.S. Cl. ................... 435/167; 435/166; 435/170; 435/176; 435/253
[58] Field of Search ............ 435/167, 166, 253, 170, 435/176

[56] References Cited

U.S. PATENT DOCUMENTS 1,940,944 12/1933 Fisher et al.
4,032,407 6/1977 Scott et al. ................. 435/176
4,332,904 6/1982 Kurane et al. ............... 435/253

FOREIGN PATENT DOCUMENTS 0073599 6/1981 Japan .................... 435/167
2107735 5/1983 United Kingdom ........... 435/167

OTHER PUBLICATIONS

The Condenced Chemical Dictionary, 10th Ed., New York, Van Nostrand Reinhold Co., Inc., 1981, pp. 179–180.

Lawrence Berkeley Laboratory, "Proceedings of a Workshop on Environmental Impacts of Marine Biomass", Final Report, Feb.–Oct. 1981.

Timothy G. Shea, et al, "Kinetics of Hydrogen Assimilation in Methane Fermentation", Aug. 1968, PB-217,394.

J. W. Rudd & C. D. Taylor, "Methane Cycling in Aquatic Environments", in *Aquatic Microbiology*, vol. 2, 1980, pp. 77–150.

D. L. Wise, et al, "Biomethanation: Anaerobic Fermentation of $CO_2$, $H_2$, & CO to Methane", in *Biotechnology and Bioengineering*, vol. XX, pp. 1153–1172, 1978.

*Primary Examiner*—David M. Naff
*Assistant Examiner*—William J. Herald
*Attorney, Agent, or Firm*—Kolisch, Hartwell & Dickinson

[57] ABSTRACT

Methane is produced by dissolving mineral carbonate in water to produce dissolved carbon dioxide which is converted to methane by anaerobic methanogenic bacteria in the presence of hydrogen gas supplied to the water. Preferably, the mineral carbonate is in the form of a bed of particulate mineral carbonate with the bacteria attached thereto. The bed is submersed in the water in a closed vessel and a flow of hydrogen gas is passed through the vessel.

8 Claims, 1 Drawing Figure

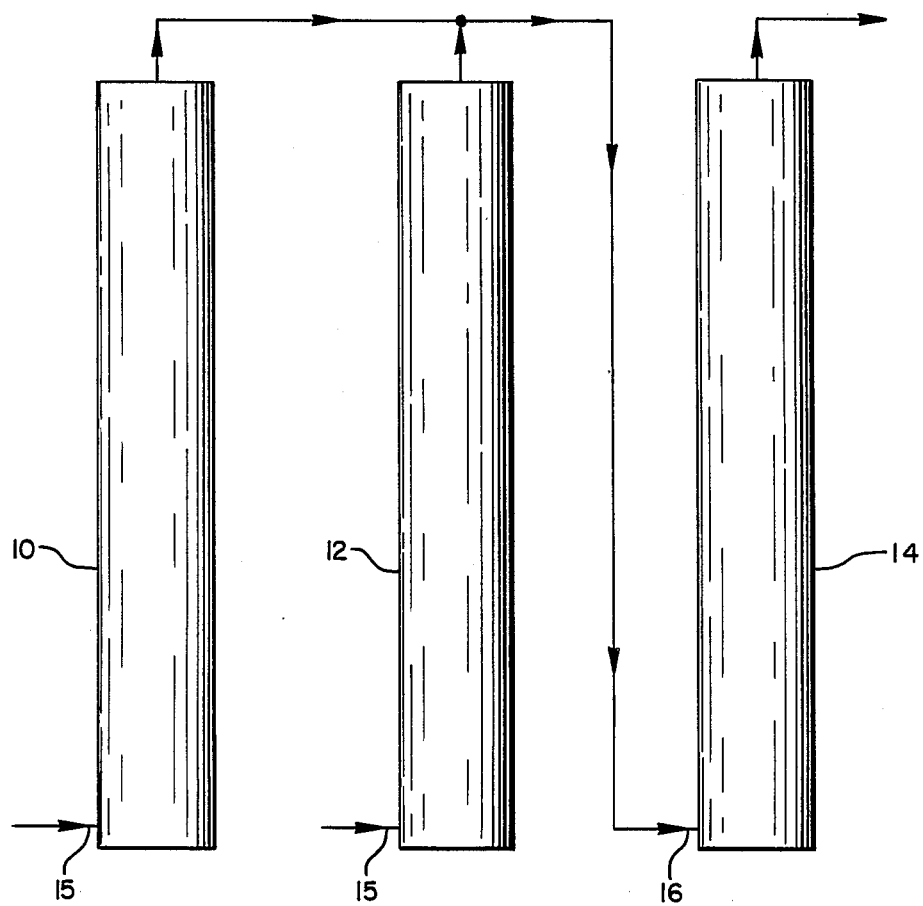

METHANE PRODUCTION

BACKGROUND AND SUMMARY OF THE INVENTION

This invention relates to a method and apparatus for producing methane, and more particularly to such a means and apparatus which relies upon methanogenic bacteria to convert a carbon source to methane.

With the world facing a dwindling supply of sources of so-called fossil fuels, many have come to believe that energy in the future will be provided through the generation and use of hydrogen. There are many problems, however, associated with this approach. For one thing, each molecule of methane possesses much more energy when combusted than a molecule of hydrogen. Natural gas is essentially methane, and all our natural gas lines are geared to the transport of methane rather than hydrogen. Hydrogen is a far more explosive material than methane. While methane technology has been fairly well developed, fairly little has been perfected in connection with hydrogen technology. Hydrogen, therefore, should be converted to methane. The need, therefore, exists for a methane generation process which is practical, nonlabor intensive, sanitary, efficient, and, in essence, provides a renewable source of methane.

The production of methane using methanogenic bacteria is not new. However, serious drawbacks are associated with known techniques for producing methane in this manner. One process which has received considerable attention in recent years is what is referred to herein as a marine biomass process, wherein an organic material such as kelp, through the action of bacteria in a fermentation process, is first broken down into simpler organic components, with these simpler components than being further broken down to materials such as acetate which are converted through further reactions with bacteria to methane. Unfortunately, however, the use of kelp or similar materials tends to be rather expensive, which becomes readily apparent when problems associated with kelp growing, harvesting, fermenting, and the elimination of waste end products, are taken into consideration. Because of the slow and inefficient nature of the process, the approach, at this time, does not appear to offer a commercially practical manner of producing methane. Marine biomass conversion is discussed in some detail in "Proceedings of a Workshop on Environmental Impacts of Marine Biomass", prepared by Lawrence Berkeley Laboratory, University of California, for Gas Research Institute, 8600 West Bryn Maur Mayr Avenue, Chicago, Ill.; (Final Report; February-October, 1981).

Another biological process for methane production is disclosed in U.S. Pat. No. 1,940,944. The process of this patent transforms carbon monoxide and hydrogen present in illuminating gas to methane, the gas being introduced to a stoppered flask which has within it a bacteria deposit. Producing methane from gaseous carbon monoxide introduces the obvious problem of providing a proper source of the gaseous carbon monoxide, and providing reaction vessels of sufficient size to handle the large volumes of gas needed to produce commercial quantities of methane.

Anaerobic fermentation of organic wastes has also been studied which is related to the naturally occurring methane production which occurs, for instance, in sediment found in rivers, swamps and bays. Studies have indicated that methane production in an anaerobic fermentation of organic waste may largely be due by reason of metabolism of materials such as acetic and propionic acids, these materials showing increased concentrations in failing fermentations. Such studies have made it appear that hydrogen and acetate metabolism by methanogenic bacteria may be related energetically, and that the presence of an excess of hydrogen may exert an inhibitory effect on the decomposition of acetate. Reference is made to "Kinetics of Hydrogen Assimilation in Methane Fermentation" by Timothy G. Shea et al., August, 1968, distributed by National Technical Information Service, U.S. Department of Commerce, 5285 Port Royal Road, Springfield, Va. In this type of process, as in a marine biomass process, many competing complex reactions are occurring, thus introducing problems in controlling operating conditions whereby significant amounts of methane are produced in a fast and efficient manner.

Generally, an object of this invention is to provide a unique process for producing methane utilizing methanogenic bacteria which obviates or minimizes many of the problems associated with processes such as those described above.

More particularly, the invention includes amongst its objects producing methane through bacteria reactions utilizing as a carbon source a water-dissolved mineral carbonate. The carbonate equilibrates in water producing dissolved carbon dioxide and the solution is essentially free from carbon compounds subject to microbial methanogenic reaction in reactions which are competitive with metabolic reduction of carbon dioxide.

More particularly, the invention contemplates the utilization of mineral carbonates as the source of carbon dioxide which have limited solubility (such term as used herein, referring to solubility of less than about 0.1 grams per 100 milliliters of water at 15° C.). A bed of such material when submerged in a volume of water functions continuously to supply to the water dissolved carbon dioxide available for conversion to methane. As carbon dioxide is used up by converting to methane, additional carbonate is dissolved. The undissolved mass of material in the bed, in addition, provides attachment sites for the methanogenic bacteria which are reacting to convert the carbon dioxide to methane.

This invention further contemplates a proces wherein methanogenic bacteria within a volume of water confined within a vessel continuously produce methane, the hydrogen needed for supplying the energy source for such conversion being introduced at least periodically (ordinarily continuously) by introducing a flow of gas into the vessel, and carbon dioxide being supplied continuously through dissolution of mineral carbonate.

Further contemplated in the invention is the continuous introduction of water to the vessel containing the methanogenic bacteria, and withdrawal of water from such vessel of water which is displaced by the introduced water. In this manner, the mineral ion content of the water is held relatively constant. The water displaced and containing mineral ions produced by the dissolving of the mineral carbonate reacts with carbon dioxide present in the air to reproduce the mineral carbonate which may then be reused in the production of methane.

These and other objects and advantages are attained by the invention, which is described hereinbelow in conjunction with the accompanying drawing, which illustrates, in simplified form, apparatus usable in practicing the invention.

DETAILED DESCRIPTION OF A PREFERRED EMBODIMENT OF THE INVENTION

In accordance with the present invention, methane is produced through the reduction of carbon dioxide dissolved in water by methanogenic bacteria. The dissolved carbon dioxide is produced by dissolving a mineral carbonate in water. Since the carbon source is essentially carbon dioxide produced by the dissolving of the mineral carbonate, eliminated from the methanogenic react on mixture are complex organic compounds containing carbon introducing competing non-methanogenic reactions. Essentially the only reaction which occurs is the simple and efficient microbial reaction formally represented by the following equation:

$$4H_2 + CO_2 \rightarrow CH_4 + 2H_2O$$

The mineral carbonate which is employed is preferably one of limited solubility, i.e., less than about 0.1 gms per 100 mls of water at 60° F. (15° C.). By using a carbonate of limited solubility, a number of advantages follow. For one thing, a fermentation tank may be prepared comprising a vessel, a column of such carbonate within it, water submerging the column of carbonate, and a colony of methanogenic bacteria. The solid carbonate in the column continuously supplies dissolved carbon dioxide to the water as such is depleted through the production of methane and, furthermore, serves as sites of attachment for the bacteria as they perform their methane-producing function. The usual mineral carbonates of limited solubility are nontoxic to the methanogenic bacteria. Furthermore, as exemplified by calcium carbonate, such is a relatively available material present in abundant supply in all areas of the world at low cost. Additionally, as will become apparent from a further reading of the description of this invention, when a carbonate such as calcium carbonate is employed, the carbonate is reclaimable, in the sense that an aqueous solution containing a high concentration of calcium ion (which results by reason of the production of methane) is quickly converted to calcium carbonate on exposure to carbon dioxide in the air. Furthermore, high solubility carbonates, as exemplified by sodium, potassium and lithium carbonates, as compared to those of limited solubility, tend to be highly corrosive and toxic, meaning that were the high solubility carbonates employed, specially designed equipment would be required in their handling.

Illustrative of mineral carbonates that are advantageously used in practicing the instant invention are those materials which are principally calcium carbonate such as calcareous shells, coral, calcite (including hydrates of calcium carbonate), limestone and dolomite. Further exemplary of carbonate materials employable are aragonite (a mixture of calcium and magnesium carbonates), magnesite (principally magnesium carbonate), rhodocrosite (magnesium carbonate) and witherite (barium carbonate).

When a column of crushed carbonate, such as calcium carbonate, is prepared in a tank, and such is submersed in water, a limited amount of the calcium carbonate dissolves according to the following equation:

$$Ca\, CO_3 \rightleftharpoons Ca^{++} + CO_3^{--}$$

An ionic equilibrium is set up in the aqueous medium producing bicarbonate and carbon dioxide, as exemplified by the following equations:

$$CO_3^{--} + H^+ \rightleftharpoons HCO_3^-$$

$$HCO_3^- + H^+ \rightleftharpoons H_2O + CO_2$$

If the water within the tank is acidified (which is not necessary for methane production), usually with any inorganic acid such as HCl, H$_2$SO$_4$, etc., to obtain a pH level within the range of 1 to 7 (normally 3.5 to 7), the equilibrium is adjusted tending to produce an increase in the carbon dioxide produced. As the carbon dioxide is used up, more carbonate dissolves, with the production of more bicarbonate and carbon dioxide. While continuously providing carbon dioxide, as such is depleted by the action of the methanogens, as already briefly indicated, the crushed relatively insoluble carbonate also serves as sites for the attachment of the methanogens producing the methane.

The water which is employed can be either fresh water, brackish or sea water. In the case of the latter, the water used itself will provide extra carbonates, bicarbonates and carbon dioxide. Tropical surface sea water, for instance, many times is supersaturated with calcium carbonate. Ordinarily, the use of sea water only, and relying upon the dissolved mineral carbonate with such contained as the sole source of carbon dioxide, is not practical, by reason of the large flows of sea water that would be required to introduce the necessary carbon source for conversion to methane.

The aqueous medium which is utilized, i.e., water together with any acid introduced to lower the pH of the system, need not be circulated or flowed through the tank to obtain production of methane. However, optimum production results when there is a circulation or flow of such medium through the tank. Further explaining, in the production of methane from a mineral carbonate such as calcium carbonate, as carbon dioxide is used up, there is an increase in the concentration of calcium ions in the aqueous medium, which tends to raise the pH of the system above the level resulting in optimal growth of the methanogenic bacteria within the system. By circulating or flowing aqueous medium through the system, calcium ions tend to be removed continuously. Use may be made of the effluent water coming from fermentation tanks, as already briefly discussed, in regenerating carbonate. When such effluent water is exposed to the atmosphere, calcium ions combine with carbon dioxide in the air, to produce more caronate which precipitates and is recoverable for reuse. Ordinarily, the amount of water or aqueous medium circulated through a fermentation tank need not exceed, on a daily basis, the volume of the tank.

The aqueous medium which is circulated through the fermentation vessel or tank may, in addition to acid, contain a small amount of organics such as yeast extract, to aid in the establishment of anaerobic conditions in the tank and to provide nutrients for the microorganisms, i.e., methanogenic bacteria which produce the methane. The use of such nutrients is desirable, therefore, particularly during the start-up phase when colony of bacteria is being established within a reaction vessel. Once a colony is established, the nutrient need not be present, since the energy which the methanogenic bacteria utilize in producing methane is derived from the hydrogen which is supplied to the fermentation tank.

Further explaining, organics in the form, for example, of yeast extract may be added to the fermentation tank, especially during the initial start-up stage, to give the microorganisms within the fermentation tank a faster start. The yeast extract supplies vitamins and other trace nutrients that the methane formers otherwise would have to synthesize. Once the process is started and the colony established, no additional organics are required for either fresh water or sea water systems. The introduction of natural waters to the system can supply the nutrients to the microorganisms once the methanogenic bacteria are established in the fermentation tank. However, this does not mean that the presence of additional organics will not aid the process. Microbial methanogenic production of methane is strictly anaerobic, and therefore the presence of organic material will aid in the removal of oxidizing compounds from the feed water, thus maintaining proper reduced conditions. Further, the addition of organics will still supply vitamins and other trace nutrients for the organisms that produce the methane, which they could synthesize, but this requires energy and therefor tends to be less efficient.

Hydrogen is supplied to the fermentation tank together with the inflowing water, and as already indicated, such is used by the bacteria to reduce the carbon dioxide to produce methane, as indicated by the microbial reaction set forth above.

The rate of flow of hydrogen into the fermentation tank is subject to variation. At a relatively low flow rate, methane production is not as high as would be obtainable with a higher flow rate. By carrying out the process utilizrng super-atmospheric pressure in the fermentation tank, the solubility of hydrogen in the aqueous medium increases, and bubbles of hydrogen and forming methane passing upwardly through the column of carbonate in the tank tend to have smaller size, permitting the use of a higher hydrogen flow rate into the system. A flow rate of hydrogen on a daily basis exceeding 600 times the volume of the fermentation tank normally would not be employed.

Temperatures and pressures utilized are subject to variation as would be readily apparent to one familiar with the action of anaerobic bacteria. Methane production has been carried out successfully at atmospheric pressure and at pressures approximating three atmospheres. The usual temperatures that one might expect to employ in methane production range from approximately 2° to 75° C., depending on the strain of methogenic bacteria used. There is an advantage in using temperatures approximating the normal atmospheric temperature of the locale where the methane production is taking place, as such eliminates the need for insulation, and heat applying or heat extraction equipment. However, some elevation of temperatures may be used to optimize the production of methane.

Methanogenic bacteria which are taxonomically described species of methanogens in pure culture comprise: *Methanobacterium arbophilicum, M. formicicum, M.ruminantium, M. mobile, M. thermoautotrophicum, Methanospirillum hungatii, Methanococcus vannielii* and *Methanosarcina barkerii*. All of the above are nutritionally simple and all use hydrogen as an energy source in reducing carbon dioxide to methane. Such methanogens are usable in practicing the instant invention. In actual practice, the methanogen species that are used may be derived from natural sources such as fresh or salt water, marsh or bay systems. If methane production is to be performed using fresh water, methanogenic bacteria such as are found in a fresh water bay sediment system may be initially employed in inoculating a fermentation tank. On the other hand, if production is to performed using salt water, methanogens present in a marine sediment may be used in the initial inoculation. After inoculation, and with anaerobic conditions established, hydrogen supplied as a source of energy, and carbon dioxide from carbonates supplied as a source of carbon, incubation proceeds with a population of anaerobic methanogenic bacteria becoming established which is specific to reduction of carbon dioxide to methane under the operating conditions established for the fermentation tank.

The following examples further illustrate the invention, the examples having been included for the purposes of illustration and not by way of limitation.

EXAMPLE I

A fermentation tank or vessel was prepared from a pipe made of inert material (such as polycarbonate or polyvinyl chloride). The pipe was 1.5 m. long and had an internal diameter of approximately 6 cm. The pipe was fitted with a fritted glass diffuser adjacent its bottom end, an inlet line connecting to the interior of the pipe below this diffuser, and an exhaust line connecting with the pipe adjacent the top end of the pipe. Stoppers closing off the bottom and top ends of the pipe produced the completed fermentation tank.

3,500 gm. cf crushed oyster shells (approximate average size of 5 to 7 mm.), when introduced into the tank, produced a column that substantially filled the tank to a point directly below the exhaust line. Also introduced into the tank was approximately 1 liter of water from Yaquina Bay, located on the shoreline of Oregon, and 50 gm. of sediment from the same location. Further introduced was 0.5 gm yeast extract. The tank after being so assembled was purged for 30 minutes by introducing hydrogen through the inlet described, to produce a flow of hydrogen of 50 cc per minute. After purging, the hydrogen flow was reduced to 12 cc per hour. The system so described was then operated at room temperature (21° -25° C.) for a period of approximately 11 days.

Gas exhausted from the outlet at the top of the column was analyzed for the presence of hydrogen, using a Hewett-Packard 5840A gas chromatograph fitted with a flame ionization detector. Methane production was noted after approximately 1 day of operation. After 11 days, the methane produced constituted approximately 0.09% of the gas exhausted from the system. In this discussion, gas percentages indicated are volume percentages.

EXAMPLE II

An aqueous medium comprising sea water, concentrated HCl, and yeast extract, in the following set forth proportions, was prepared:

sea water, 1.0 liter
HCl, 5.0 ml.
yeast extract, 0.1 gm.

This aqueous medium was circulated through the tank described in Example 1 together with hydrogen. The flow rate of hydrogen was 1.2 l. per day. The flow rate of aqueous medium was 0.43 l. per day. After a period of approximately 7 months, the gas exhausting from the top of the tank was determined to be approximately 73.5% methane. Subsequently, the hydrogen flow was increased to 1.85 l. per day. After approximately a week the methane concentration of the gas leaving the top of the tank was essentially 100%.

The tank was then operated using a hydrogen flow rate through the tank of 2.4 l. per day. After a short period of time, gas exhausting from the top of the column was found to be essentially pure methane.

EXAMPLE III

Apparatus was prepared as illustrated in the drawing accompanying this specification. Thus, two primary fermentation tanks such as those shown at 10 and 12 were prepared from pipes 2 mm. long and having internal diameters of approximately 15 cm. A secondary fermentation 14 tank was prepared from a similar piece of pipe. 45.3 kg of crushed oyster shells were introduced to each tank which substantially filled the tank. The tanks were closed off at top and bottom by caps. Provision was made for introducing aqueous medium and hydrogen to inlets 15 adjacent to the base of each of the primary fermentation tank . Outlets adjacent to the top of these two primary fermentation tanks were jointly connected through conduit structure to an inlet 16 adjacent to the base of a secondary fermentation tank. Thus, the secondary fermentation tank received the aqueous medium, hydrogen, and methane discharged from the two primary tanks.

The tanks were filled with the aqueous medium described in Example II, and allowed to stand while feeding hydrogen to the two primary tanks using a flow rate to each of 11 l. per day. After 2 days, anaerobic conditions were established within the tanks. All the tanks were then inoculated, by injecting into each 100 ml. of the methanogenic culture obtained from the tank described in Example II. This injection was repeated daily for three days. After the final injection, the hydrogen fow rate to each primary fermentation tank was established at 11 l. per day. The flow rate of aqueous medium to each of the primary fermentation tanks was established at 1.58 l. per day. The process was performed at atmospheric pressure and room temperature. The following table indicates the methane production obtained by the above-described apparatus, with measurements taken at the head space of the respective columns. As the table indicates, the hydrogen flow rate on the 17th day was increased to 30 l. per day, and on the 27th day was increased to 35 l. per day.

The methanogenic culture utilized in the above inoculation is available from the permanent collection of the American Type Culture Collection, 12301 Parklawn Drive, Rockville, Md., 20852, ATCC designation 39210.

TABLE I

| | | Percent Methane | | |
|---|---|---|---|---|
| Day | $H_2$ flow (l./day) | 1st Primary Fermentation Tank | 2nd Primary Fermentation Tank | Secondary Fermentation Tank |
| 1st | 11 | 49.7 | 89.1 | 43.4 |
| 3rd | 11 | 82.2 | 72.8 | 64.3 |
| 6th | 11 | 93.7 | 32.6 | 84.8 |
| 11th | 11 | 100 | 33.5 | 95.8 |
| 13th | 11 | 97.8 | 69.1 | 100 |
| 17th | 30 | 68.2 | 50.1 | 91.2 |
| 21st | 30 | 46.0 | 91.6 | 98.9 |
| 22nd | 30 | 45.1 | 81.0 | 99.9 |
| 27th | 35 | 6.6 | 15.8 | 30.9 |
| 36th | 35 | 30.2 | 10.5 | 87.3 |
| 49th | 35 | 90.0 | 52.9 | 100 |

Effluent water leaving the secondary fermentation tank was allowed to stand in the open atmosphere. Such resulted in calcium carbonate precipitating from the water.

EXAMPLE IV

Three different fermenation tanks were prepared, each from pipe having an internal diameter of approximately 15 cm. and each 3 mm. long. Each was wrapped with heat tape and fiberglass insulation for temperature control. Each was provided with an outlet adjacent its top fitted with a solenoid operated pressure valve for pressure control. Each was provided adjacent its base with an inlet for introducing hydrogen and/or aqueous medium. 68 kg. of crushed oyster shells introduced to each tank substantially filled the tank.

The various tanks were filled with aqueous medium as described in Example II, and allowed to set for a period of two days with a hydrogen flow through each column established at 10 l. per day. After a period of 2 days, when anaerobic conditions had been established, each column was inoculated with 100 ml. of the methanogenic culture produced in the column of Example II, daily, for a period of three consecutive days. Flow of aqueous medium through each column was then established at a rate of 1.87 l. per day.

The following table illustrates the methane production obtained from the 3 tanks. As the table indicates, on the 7th day the pressure within the three columns was increased to 1.3 atmospheres from atmospheric pressure. The temperature in all the columns was maintained at 25° C. Hydrogen flows are indicated on a volumetric basis at atmospheric pressure and temperature conditions.

TABLE II

| | | | | Col. 1 | | Col. 2 | | Col. 3 | |
|---|---|---|---|---|---|---|---|---|---|
| Day | Pressure (atm.) | $H_2$ flow (l./day) | Media flow (l./day) | % Methane | Temp. (°C.) | % Methane | Temp. (°C.) | % Methane | Temp. (°C.) |
| 1st | 1 | 10 | 1.87 | 0 | 25 | 0 | 25 | 0 | 25 |
| 6th | 1 | 10 | 1.87 | 0.141 | 25 | 0.144 | 25 | 0.134 | 25 |
| 7th | 1.3 | 10 | 1.87 | 3.94 | 25 | 10.26 | 25 | 8.62 | 25 |
| 10th | 1.3 | 10 | 1.87 | 6.08 | 25 | 12.79 | 25 | 9.24 | 25 |
| 13th | 1.3 | 10 | 1.87 | 11.56 | 25 | 15.81 | 25 | 18.13 | 25 |
| 17th | 1.3 | 10 | 1.87 | 22.81 | 25 | 27.48 | 25 | 22.10 | 25 |

The operation of columns 1 and 2 was continued with raising of the temperature of column 2 to 35° C. on the 27th day. On the 30th day the feed of hydrogen was increased to 20 l. per day and on the 32nd day the feed of hydrogen was increased to 40 l. per day. On the 37th day, the pressure in the respective columns was increased to 3 atmospheres. On the 49th day, the flow of aqueous media was increased to 3.02 l. per day. On the 70th day, the feed of aqueous media was increased 4.61 l. per day. The following table summarizes the percent methane obtained from the gaseous exhaust of the respective columns over the time period indicated.

TABLE III

| Day | Pressure (atm.) | $H_2$ flow (l./day) | Media flow (l./day) | Col. 1 % Methane | Col. 1 Temp. (°C.) | Col. 2 % Methane | Col. 2 Temp. (°C.) |
| --- | --- | --- | --- | --- | --- | --- | --- |
| 27th | 1.3 | 10 | 1.87 | 47.15 | 25 | 50.01 | 35 |
| 29th | 1.3 | 10 | 1.87 | 72.89 | | 85.53 | |
| 30th | 1.3 | 20 | 1.87 | 87.18 | | 95.89 | |
| 31st | 1.3 | 20 | 1.87 | 97.39 | | 100 | |
| 32nd | 1.3 | 40 | 1.87 | 100 | | 49.97 | |
| 35th | 1.3 | 40 | 1.87 | 37.54 | | 23.08 | |
| 37th | 3.0 | 40 | 1.87 | 10.35 | | 14.05 | |
| 43rd | 3.0 | 40 | 1.87 | 20.29 | | 38.61 | |
| 49th | 3.0 | 40 | 3.02 | 28.39 | | 14.97 | |
| 52nd | 3.0 | 40 | 3.02 | 35.37 | | 20.95 | |
| 55th | 3.0 | 40 | 3.02 | 74.16 | | 45.79 | |
| 58th | 3.0 | 40 | 3.02 | 100 | | 76.48 | |
| 59th | 3.0 | 40 | 3.02 | 100 | | 83.64 | |
| 61st | 3.0 | 40 | 3.02 | 86.74 | | 100 | |
| 63rd | 3.0 | 40 | 3.02 | 61.22 | | 100 | |
| 64th | 3.0 | 40 | 3.02 | 46.28 | | 100 | |
| 70th | 3.0 | 40 | 4.61 | 38.42 | | 58.25 | |

As the above table indicates, a considerable increase in methane production results from a pressure increase. This, most likely, results by reason of the increased solubility of hydrogen in water with increased pressure, and due to the reduction in bubble size of the methane and hydrogen as such travel upwardly in the respective tanks, thereby increasing the exposure of unreduced hydrogen to the methanogenic bacteria in the tank.

The process above-described has several advantages. For one thing, it should be noted that the source of carbon in the process, i.e., the mineral carbonate, is an extremely inexpensive source of material. With sea water employed, the carbonates, bicarbonates and carbon dioxide dissolved in sea water are added sources of carbon dioxide. The equipment required and the method of the invention is relatively simple. Once operting conditions have been established in a fermentation tank, methane production will continue uninterruptedly, with minimal supervision required.

A colony of methanogenic bacteria once established in a fermentation tank becomes selective to the operating conditions present, then the colony will continue to operate effectively with such conditions are maintained.

The process contemplated is far less complicated and time consuming then marine biomass systems which have been proposed to date. By utilizing a mineral carbonate as the source of carbon, competing complex methanogenic reactions such as occur with the usual biomass systems are substantially eliminated.

While modifications of the invention have been described, it is desired not to be limited to specifics of the invention as herein disclosed, but to cover all such modifications and variations as would be apparent to one skilled in the art.

It is claimed and desired to be secured by Letters Patent:

1. A method of producing methane gas comprising:
providing in a closed vessel (a) a bed of particulate mineral carbonate having a solubility of less than 0.1 gms per 100 mls of water at 15° C., (b) a volume of water submersing the bed of mineral carbonate, and (c) a population of anaerobic methanogenic bacteria specifically adapted for the conversion of carbon dioxide to methane attached to the particulate mineral carbonate in said bed,
and with the vessel so provided (d) circulating water through the vessel and (e) passing a flow of hydrogen gas through the vessel, the mineral carbonate in said bed through dissolution introducing dissolved carbon dioxide and mineral ions to the water within the vessel, the methanogenic bacteria utilizing the energy supplied by the hydrogen gas to convert the dissolved carbon dioxide to methane gas, the water circulated through the vessel removing mineral ions introduced by dissolution of the mineral carbonate, and
withdrawing from the vessel the methane gas so produced.

2. The method of claim 1, wherein water after circulation through the vessel is exposed to the air, with the precipitation from the water of mineral carbonate formed by the reaction of carbon dioxide in the air with mineral ions in the water.

3. The method of claim 1 wherein the contents of the vessel are maintained at a superatmospheric pressure.

4. The method of claim 3, wherein water after circulation through the vessel is exposed to the air with the precipitation from the water of mineral carbonate regenerated by the reaction of carbon dioxide in the air with mineral ions in the water.

5. The method of claim 1, wherein the mineral carbonate is calcium carbonate, and the population of bacteria is started on said bed by submersing the bed in water containing organic nutrients for the bacteria.

6. A method of producing methane gas which comprises:
providing a bed of particulate calcium carbonate in a closed vessel and submersing the bed within the vessel in water,
establishing a population of anaerobic methanogenic bacteria specifically adapted for the conversion of carbon dioxide to methane attached to the particulate carbonate in said bed, introducing into the vessel a flow of hydrogen gas which gas enters the vessel and travels through the water and over the submersed bed of carbonate material, the calcium carbonate through dissolution introducing dissolved carbon dioxide to the water within the vessel and the methaogenic bacteria utilizing the energy supplied by the hydrogen gas flowing over the submersed bed to convert the dissolved carbon dioxide to methane gas, and withdrawing from the vessel the methane gas so produced.

7. The method of claim 6, which further comprises circulating water through the vessel, the calcium carbonate of the bed on dissolution introducing to the water within the vessel calcium in addition to dissolved carbon dioxide, and circulating of the water being effective to remove such calcium ions.

8. The method of claim 6, wherein the population of methanogenic bacteria is established by depositing bacteria within the vessel and supplying the water submersing the bed with an organic nutrient for the bacteria.

* * * * *